United States Patent [19]

Nakamoto et al.

[11] Patent Number: 4,521,417
[45] Date of Patent: Jun. 4, 1985

[54] GERANYLGERANYLACETAMIDE COMPOUNDS HAVING A PIPERAZINE RING, SALTS THEREOF, PHARMACEUTICAL COMPOSITIONS CONTAINING SAID COMPOUNDS, AND METHOD OF TREATING ULCERS IN MAMMALS

[75] Inventors: Hiromasa Nakamoto, Takaoka; Michitaka Ogawa, Uozu; Muneo Kobayashi, Toyama; Yuki Nogami, Toyama; Kazuo Kumamoto, Toyama; Hiroko Murakami, Toyama; Yoichi Ninagawa, Hasaki; Yoshiaki Omura, Mitsu; Masao Mizuno, Kurashiki, all of Japan

[73] Assignees: Nihon Iyakuhin Kogyo Co., Ltd., Toyama; Kuraray Co., Ltd., Kurashiki, both of Japan

[21] Appl. No.: 501,391

[22] Filed: Jun. 6, 1983

[30] Foreign Application Priority Data

Jun. 7, 1982 [JP] Japan ................... 57-96341

[51] Int. Cl.³ ................ A61K 31/495; C07D 241/04
[52] U.S. Cl. .................... 514/255; 544/386; 544/391
[58] Field of Search ............ 544/386, 391; 424/250

[56] References Cited

U.S. PATENT DOCUMENTS

| 3,646,036 | 2/1972 | Laos | 424/250 |
| 3,666,780 | 5/1982 | Calame et al. | 544/386 |
| 4,151,357 | 4/1979 | Mishima et al. | 544/391 |
| 4,379,928 | 4/1982 | Theodoropulos | 544/386 |

FOREIGN PATENT DOCUMENTS 55-129275 10/1980 Japan .

Primary Examiner—Glennon H. Hollrah
Assistant Examiner—James H. Turnipseed
Attorney, Agent, or Firm—Wenderoth, Lind & Ponack

[57] ABSTRACT

A geranylgeranylacetamide compound having a piperazine ring represented by the following formula (I)

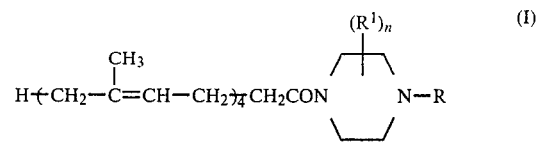

wherein R represents a member selected from the class consisting of a hydrogen atom, $C_1$–$C_5$ alkyl groups which are unsubstituted or mono-substituted by a halogen atom, $C_2$–$C_5$ alkenyl groups and $C_7$–$C_8$ aralkyl groups, $R_1$ represents a $C_1$–$C_3$ alkyl group, and n represents 0, 1 or 2, and a pharmaceutically acceptable acid addition salt thereof. The aforesaid compound can be prepared by reacting geranylgeranylacetic acid or its reactive derivative with a piperazine compound, and thereafter, if desired, transforming the free geranylgeranylacetamide compound thus obtained into its pharmaceutically acceptable acid addition salt. A pharmaceutical composition containing said compound exhibits antiulcerogenic activity, particularly excellent antipeptic ulcerogenic activity, and is useful as an agent for treating ulcers.

18 Claims, No Drawings

GERANYLGERANYLACETAMIDE COMPOUNDS HAVING A PIPERAZINE RING, SALTS THEREOF, PHARMACEUTICAL COMPOSITIONS CONTAINING SAID COMPOUNDS, AND METHOD OF TREATING ULCERS IN MAMMALS

This invention relates to novel geranylgeranylacetamide compounds having a piperazine ring and their pharmaceutically acceptable acid addition salts which exhibit antiulcerogenic activity, particularly excellent antipeptic ulcerogenic activity, and to uses of these compounds as an antipeptic ulcer agent.

More specifically, this invention relates to a geranylgeranylacetamide compound having a piperazine ring represented by the following formula

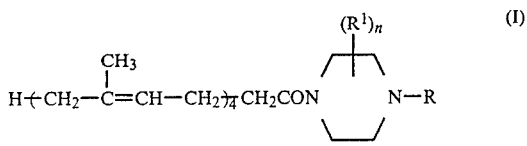

wherein R represents a member selected from the class consisting of a hydrogen atom, $C_1$–$C_5$ alkyl groups which are unsubstituted or mono-substituted by a halogen atom, $C_2$–$C_5$ alkenyl groups and $C_7$–$C_8$ aralkyl groups, $R^1$ represents a $C_1$–$C_3$ alkyl group and n represents 0, 1 or 2, and their pharmaceutically acceptable acid addition salts; and to uses of these compounds as an antipeptic ulcer agent.

This invention also relates to a process for producing the aforesaid novel compounds, and a method for treating peptic ulcer by using the aforesaid compounds.

The term "geranylgeranyl", as used herein, denotes a group of the formula

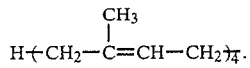

Its geometric form may be trans, cis or a mixture thereof, and formula (I) in this invention is used to include all of these cases.

It has previously been known that certain kinds of farnesylacetic acid esters and farnesylacetamides have antiulcerogenic activity (Japanese Laid-Open Patent Publication No. 129275/1980 and U.S. Pat. No. 3,646,036).

The above-cited Japanese Laid-Open Patent Publication No. 129275/1980 discloses farnesylacetamides of the following formula (A)

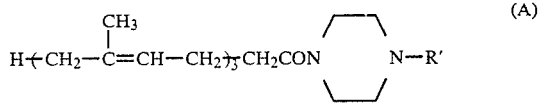

wherein R' represents a hydrogen atom or an alkyl, cycloalkyl, alkenyl, aryl or aralkyl group,
and their salts. This patent document shows a test on an indomethacine-induced ulcer (test animals, male Donryo rats; dosage 20 mg/kg, subcutaneously) using a compound of formula (A)-1 corresponding to formula (A) in which R' is $CH_3$.

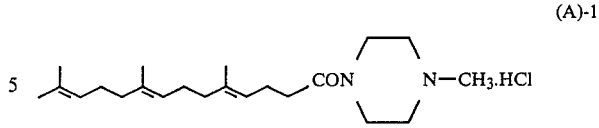

U.S. Pat. No. 3,646,036 discloses 1-farnesylacetyl-4-hydroxyalkyl-piperazines represented by the following formula

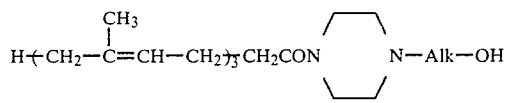

wherein Alk represents a lower alkylene radical possessing at least 2 carbon atoms,
and their salts. The patent states that these amides exhibit valuable pharmacological properties, e.g. antiulcerogenic, anti-bradykinin, anti-protozoal and anthelmintic, but fails to show any test data of their pharmacological effects.

The present inventors have conducted investigations about the development and utilization of geranylgeranylacetamide compounds which are different from the farnesylacetamides of the above-cited prior art and naturally have different pharmacological effects.

These investigations have led to the discovery that the geranylgeranylacetamide compounds having a piperazine ring represented by formula (I) and their salts, which are not described in the prior literature, can be easily synthesized in good yields, and that these novel compounds show strong antiulcerogenic activity, especially excellent anti-peptic ulcerogenic activity and are very useful as agents for the prevention, curing and repalse-prevention of ulcerogenic diseases.

It has also been found that these novel compounds have low toxicity, little side-effects and high safety, and are noteworthy as anti-ulcerogenic agents showing excellent anti-ulcerogenic activity.

It is an object of this invention therefore to provide novel geranylgeranylacetamide compounds having a piperazine ring represented by the above formula (I) or their salts.

Another object of this invention is to provide an agent for treating ulcers, especially peptic ulcer, which comprises the compound of formula (I) or its pharmaceutically acceptable salt as an active ingredient.

Still another object of this invention is to provide a process for producing the compound of formula (I) or its salt.

The above and other objects and advantages of this invention will become more apparent from the following description.

In the compound of formula (I) in accordance with this invention, examples of $C_1$–$C_5$ alkyl groups which are unsubstituted or mono-substituted by a halogen atom include $C_1$–$C_5$ alkyl groups substituted by a halogen atom such as chlorine, bromine, fluorine and iodine. The alkyl groups may be linear or branched $C_1$–$C_5$ alkyl groups such as methyl, ethyl, n-propyl, isopropyl, n-butyl, isobutyl, tert-butyl, n-pentyl, isopentyl and neopentyl. Examples of $C_2$–$C_5$ alkenyl groups for R in formula (I) are vinyl, 1-propenyl, allyl, methallyl, 1-butenyl, 2-butenyl, 3-butenyl, 1-pentenyl, 2-pentenyl, 3-pentenyl and prenyl. Examples of the aralkyl groups having 7 or 8 carbon atoms for R in formula (I) are benzyl, phenethyl, and methylbenzyl.

Examples of $C_1$–$C_3$ for R' in formula (I) include methyl, ethyl n-propyl and isopropyl.

Examples of the salts of the compounds of formula (I) include inorganic acid addition salts such as hydrochlorides, hydrobromides, sulfates and phosphates, and organic acid addition salts such as citrates, lactates, fumarates and glutamates.

Examples of the compounds of formula (I) and their pharmaceutically acceptable acid addition salts include
N-geranylgeranylacetyl piperazine,
N-methyl-N'-geranylgeranylacetyl piperazine,
N-ethyl-N'-geranylgeranylacetyl piperazine,
N-n-propyl-N'-geranylgeranylacetyl piperazine,
N-isopropyl-N'-geranylgeranylacetyl piperazine,
N-n-butyl-N'-geranylgeranylacetyl piperazine,
N-isobutyl-N'-geranylgeranylacetyl piperazine,
N-tert-butyl-N'-geranylgeranylacetyl piperazine,
N-n-amyl-N'-geranylgeranylacetyl piperazine,
N-isopentyl-N'-geranylgeranylacetyl piperazine,
N-vinyl-N'-geranylgeranylacetyl piperazine,
N-allyl-N'-geranylgeranylacetyl piperazine,
N-2-butenyl-N'-geranylgeranylacetyl piperazine,
N-prenyl-N'-geranylgeranylacetyl piperazine,
N-benzyl-N'-geranylgeranylacetyl piperazine,
N-phenethyl-N'-geranylgeranylacetyl piperazine,
2-methyl, 3-methyl, 2-ethyl, 3-ethyl, 2-propyl, or 3-propyl-N-geranylgeranylacetyl piperazine,
2,3-dimethyl, 2,5-dimethyl, 2,6-dimethyl, 2,3-diethyl, 2,5-diethyl, or 2,6-diethyl-N-geranylgeranylacetyl piperazine, and
pharmaceutically acceptable salts of these compounds with the above-exemplified inorganic or organic acids.

The compound of formula (I) and its pharmaceutically acceptable acid addition salt in accordance with this invention can be produced by a known method for synthesizing carboxylic acid amides.

According to one embodiment of the present invention, the compound of formula (I) can be produced by reacting geranylgeranylacetic acid or its reactive derivative represented by the following formula (II)

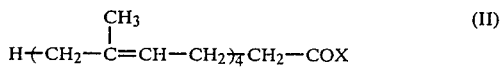

wherein X represents a hydroxyl group, a halogen atom or a lower alkoxy group, with a piperazine compound represented by the following formula (III)

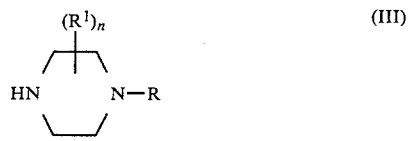

wherein R, R' and n are as defined with regard to formula (I). Conversion of the product to a salt can be easily carried out by contacting the compound of formula (I) so formed with an inorganic or organic acid of the types exemplified hereinabove.

Of the compounds of formula (II) used in the above reaction, a reactive derivative of geranylgeranylacetic acid represented by formula (II) in which X is a lower alkoxy group, i.e. a lower alkyl ester of geranylgeranylacetic acid, can be produced, for example, by reacting geranyl linalol with a lower alkyl orthoacetate in the presence of an acid catalyst. For example, methyl geranylgeranylacetate corresponding to formula (II) in which X is methoxy can be easily synthesized, for example, by reacting geranyl linalol with about 0.5 to about 10 moles, preferably about 1.0 to about 3.0 moles, per mole of geranyl linalol, of methyl orthoacetate under heat in the presence of an acid catalyst such as phosphoric acid, acetic acid or propionic acid while distilling off the resulting methanol out of the reaction system. The reaction temperature for this reaction is generally in the range of about 70° to about 170° C. Desirably, the temperature is elevated little by little as the reaction proceeds. The reaction can usually be completed in about 5 to about 24 hours although it varies depending upon the reaction temperature.

A compound of formula (II) in which X is a lower alkoxy group other than methoxy can be synthesized by the same method as above by using the corresponding lower alkyl orthoacetate. It is convenient, however, to synthesize it by transesterification of methyl geranylgeranylacetate with the corresponding lower alkanol. This transesterification reaction can be easily carried out by heating methyl geranylgeranylacetate in the lower alkanol in the presence of a known transesterification catalyst such as an alkali metal hydroxide (i.e., sodium hydroxide or potassium hydroxide) or an alkali metal alkoxide of the corresponding alkanol.

Geranylgeranylacetic acid corresponding to formula (II) in which X is a hydroxyl group can be easily obtained by hydrolyzing methyl geranylgeranylacetate which can be obtained as above, in accordance with known methods used for the hydrolysis of higher fatty acid esters. This hydrolysis reaction can be carried out, for example, by saponifying methyl geranylgeranylacetate in aqueous methanol or hydrous ethanol in the presence of an equimolar or excessive molar proportion of sodium hydroxide or potassium hydroxide, and then neutralizing the saponification product with an inorganic acid such as hydrochloric acid or sulfuric acid.

A reactive derivative of geranylgeranylacetic acid represented by formula (II) in which X is a halogen atom can be obtained, for example, by reacting geranylgeranylacetic acid with a thionyl halide such as thionyl chloride and thionyl bromide. This reaction can be carried out in accordance with known methods used for the synthesis of acid halides (for example, see a Japanese-language publication "New Experimental Chemistry Lectures", Vol. 14-II, pages 1106–1108, edited by the Chemical Society of Japan).

The piperazine compound of formula (III) can also be synthesized in accordance with known methods (see, for example, a Japanese-language publication "New Experimental Chemistry Lectures", Vol. 14-III, page 132, edited by the Chemical Society of Japan).

The compound of formula (I) in accordance with this invention can be obtained by reacting the geranylgeranylacetic acid or its reactive derivative of formula (II) with the piperazine compound of formula (III) which can be obtained as described above. To obtain a pharmaceutically acceptable acid addition salt of the compound of formula (I), the resulting compound of formula (I) is contacted with an inorganic or organic acid.

The reaction of a lower alkyl geranylgeranylacetate corresponding to formula (II) in which X is a lower alkoxy group with the compound of formula (III) can be carried out in the absence of solvent. Usually, however, it can be conveniently carried out in a solvent inert to the reaction. One mole of the lower alkyl geranylgeranylacetate may be reacted with about 0.3 to about 3.0 moles, preferably about 0.75 to about 1.5 moles, of the compound of formula (III) at a reaction temperature of, for example, about 100° to about 250° C., preferably about 150° to about 200° C. Usually, the desired reaction can be completed in about 2 to about 48 hours although this time may vary depending upon the reaction temperature used.

The reaction of a compound of formula (II) in which X is a halogen atom (to be referred to as a substituted acetyl halide) with the compound of formula (III) may be carried out in the presence of a solvent inert to the reaction, such as toluene and xylene, at a temperature of about 50° to about 150° C., preferably about 100° to about 140° C. The suitable amount of the compound of formula (III) is about 0.5 to about 2.0 moles, preferably about 0.75 to about 1.5 moles, per mole of the substituted acetyl halide. The amount of the solvent used may be chosen properly. For example, it is about 5to about 100 times, preferably about 10 to about 50 times, the weight of the substituted acetyl halide. Preferably, a predetermined amount of the compound of formula (III) is dissolved in the solvent, and the substituted acetyl halide is added and reacted at an elevated temperature with stirring. At this time, it is preferred to add a predetermined amount of the substituted acetyl halide in several small portions, or to add it dropwise gradually rather than to add it all at a time. The desired reaction can be completed by stirring the reaction mixture for a period of, for example, about 0.1 to about 5 hours under the above reaction conditions.

The reaction of geranylgeranylacetic acid corresponding to formula (II) in which X is OH with the compound of formula (III) can be carried out by contacting them usually in the presence of a condensing agent such as N,N'-dicyclocarbodiimide, N,N'-diethylcarbodiimide, a trialkyl phosphite, an alkyl polyphosphate, phosphorus oxychloride, oxallyl chloride or tosyl chloride. The reaction can be carried out, for example, at a temperature of about 0° C. to about 50° C. For example, equimolar proportions of geranylgeranylacetic acid and the compound of formula (III) are dissolved in a non-aqueous solvent such as chloroform, and an equimolar proportion of N,N'-dicyclocarbodiimide is added. The mixture is stirred at 0° C. for 3 hours, and then left to stand overnight at room temperature, whereby the reaction can be completed.

The compounds of formula (I) and their pharmaceutically acceptable acid addition salt in accordance with this invention show excellent anti-ulcerogenic activity, and are useful for the prevention, therapy and repalse-prevention of peptic ulcer such as gastric ulcer and duodenal ulcer. In addition, these compounds have low toxicity.

Thus, according to this invention, there is also provided a pharmaceutical composition for treatment of peptic ulcers, said composition being composed of (1) an amount, effective for treatment of peptic ulcer, of a geranylgeranylacetamide compound having a piperazine ring represented by the following formula (I)

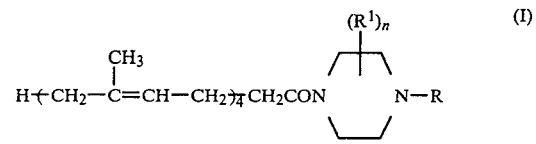

wherein R represents a member selected from the class consisting of a hydrogen atom, $C_1$-$C_5$ alkyl groups which are unsubstituted or mono-substituted by a halogen atom, $C_2$-$C_5$ alkenyl groups and $C_7$-$C_8$ aralkyl groups, $R^1$ represents a $C_1$-$C_3$ alkyl group and n represents 0, 1 or 2, or its pharmaceutically acceptable acid addition salt, and (2) a pharmaceutically acceptable diluent or carrier.

The present invention further provides a method for treating peptic ulcer which comprises administering an effective amount of the compound of formula (I) or its pharmaceutically acceptable acid addition salt to a patient with peptic ulcer or a mammal suspected of having peptic ulcer.

The pharmaceutical composition of this invention for the treatment of peptic ulcer can be formulated into various dosage forms by using means known per se. For example, the dosage forms may be those suitable for oral administration such as tablets, granules, powders, coated tablets, hard capsules, soft capsules and oral liquid preparations and those suitable for injection such as suspensions, liquid preparations, and oily or aqueous emulsions.

The pharmaceutical composition of this invention may contain various pharmaceutically acceptable liquid or solid diluents or carriers known per se. Examples of such diluents or carriers include syrup, gum arabic, gelatin, sorbitol, tragacanth, polyvinylpyrrolidone, magnesium stearate, talc, polyethylene glycol, silica, lactose, sucrose, corn starch, calcium phosphate, glycine, potato starch, calcium carboxymethylcellulose, sodium laurylsulfate, water, ethanol, glycerol, mannitol and phosphate buffer.

The pharmaceutical composition of this invention may further include adjuvants conventionally used in the field of pharmaceutical production, such as coloring agents, flavors, corrigents, antiseptics, dissolution aids, suspending agents and dispersing agents.

The pharmaceutical composition of the invention may be in the form filled in a large dosage container as well as in a fixed dosage form such as tablets, capsules, coated tablets, ampoules, etc. exemplified hereinabove.

The pharmaceutical composition of the invention contains an amount, effective for treatment of peptic ulcer, of the compound of formula (I) and its pharmaceutically acceptable acid addition salt. Its dosage can be varied properly depending upon the condition of the subject, the purpose of administration, etc. For example, it is about 100 to about 4,000 mg, preferably about 500 to about 2,000 mg, per day for an adult.

The pharmaceutical composition of this invention can be administered through various routes, for example orally or by injection (e.g., intravenous, subcutaneous, intramuscular). Oral administration and intravenous injection are especially preferred.

The compound of formula (I) and its pharmaceutically acceptable acid addition salt have anti-ulcerogenic activity which is much stronger than known active compounds used as anti-ulcerogenic agents, such as geranyl farnesylacetate (Gefarnate), 4-(2-carboxyethyl)-phenyl-trans-4-aminomethylcyclohexanecarboxylate hydrochloride (Cetraxate hydrochloride), and glycyrrhetinic acid hydrogen succinate, disodium salt (Carbenoxolone sodium).

Pharmacological tests were conducted on the above-mentioned known anti-ulcerogenic agents, the typical known anti-ulcerogenic compound of formula (A)-1 given hereinabove, and the compounds of formula (I) in accordance with this invention in order to examine their anti-ulcerogenic activities. The results ae shown in the following.

In these pharmacological tests, the numbers attached to the compounds of this invention correspond to the numbers of Production Examples given hereinbelow.

PHARMACOLOGICAL TEST 1

STD Wistar-strain male rats (body weight 170 to 200 g) were caused to fast for 72 hours, and then under ether anesthesia, were incised at the abdomen. The pylorus portion was ligated, and each of the test drugs was intraduodenally administered. The abdomen was closed and sewn. Eight hours later, the abdomen was cut open, and the stomach was taken out. The area of a generated ulcer was measured by a stereoscopic microscope, and the percent inhibition was calculated by comparison from a control to which the drug was not administered. The results are shown in Table 1.

TABLE 1

| Test drug | Dose (mg/Kg) | Number of animals | Percent inhibition (%) |
|---|---|---|---|
| Compound (1) | 300 | 15 | 68.2 |
| Compound (2) | 300 | 15 | 74.5 |
| Compound (3) | 300 | 15 | 70.1 |
| Compound (4) | 300 | 15 | 64.7 |
| Compound (5) | 300 | 15 | 66.5 |
| Compound (6) | 300 | 15 | 66.5 |
| Compound (7) | 300 | 15 | 67.3 |
| Compound (8) | 300 | 15 | 70.5 |
| Compound (9) | 300 | 15 | 64.0 |
| Compound (10) | 300 | 15 | 65.3 |
| Compound (11) | 300 | 15 | 66.8 |
| Compound (12) | 300 | 15 | 64.9 |
| Compound (13) | 300 | 15 | 77.1 |
| Compound (14) | 300 | 15 | 71.5 |
| Compound (15) | 300 | 15 | 80.0 |
| Gefarnate | 300 | 15 | 30.0 |
| Cetraxate hydrochloride | 300 | 15 | 27.8 |
| Carbenoxolone sodium | 300 | 15 | 60.5 |
| Comparative compound of formula (A)-1 | 300 | 15 | 53.3 |

PHARMACOLOGICAL TEST 2

STD Wistar-strain male rats (body weight 170 to 200 g) were caused to fast for 30 hours, and put in a wire cage. They were immersed in a constant temperature water tank kept at 23±1° C. to their emsistermun. Eighteen hours later, the animals were taken out, and incised at the abdomen. The stomach was cut open and examined microscopically. One hour before applying stress to the animals by water immersion, each of the test drugs was orally administered. The total length of ulcers generated in the stomach body was compared with that in a control, and the rate of inhibiting ulcer formation was calculated. The results are shown in Table 2.

TABLE 2

| Test drug | Dose (mg/Kg) | Number of animals | Percent inhibition (%) |
|---|---|---|---|
| Compound (1) | 300 | 10 | 73.8 |
| Compound (2) | 300 | 10 | 76.0 |
| Compound (3) | 300 | 10 | 68.7 |
| Compound (4) | 300 | 10 | 69.0 |
| Compound (5) | 300 | 10 | 64.0 |
| Compound (6) | 300 | 10 | 60.6 |
| Compound (7) | 300 | 10 | 64.6 |
| Compound (8) | 300 | 10 | 68.5 |
| Compound (9) | 300 | 10 | 59.0 |
| Compound (10) | 300 | 10 | 67.3 |
| Compound (11) | 300 | 10 | 65.3 |
| Compound (12) | 300 | 10 | 61.1 |
| Compound (13) | 300 | 10 | 82.8 |
| Compound (14) | 300 | 10 | 70.2 |
| Compound (15) | 300 | 10 | 80.0 |
| Gefarnate | 300 | 10 | 23.6 |
| Cetraxate hydrochloride | 300 | 10 | 31.6 |
| Carbenoxolone sodium | 300 | 10 | 8.6 |
| Comparative compound of formula (A)-1 | 300 | 10 | 45.6 |

PHARMACOLOGICAL TEST 3

STD Wistar male rats (body weight 170 to 200 g) were caused to fast for 24 hours, and indomethacine dissolved in a 5% aqueous solution of sodium hydrogen carbonate was subcutaneously administered in a dose of 40 mg/kg. Seven hours later, the animals were autopsied. Each of the test drugs was administered orally to the stomach 10 minutes before administration of indomethacine. The total length of ulcers formed was compared with that in a control, and the percent inhibition was calculated. The results are shown in Table 3.

TABLE 3

| Test drug | Dose (mg/Kg) | Number of animals | Percent inhibition (%) |
|---|---|---|---|
| Compound (1) | 200 | 10 | 66.0 |
| Compound (2) | 200 | 10 | 75.3 |
| Compound (3) | 200 | 10 | 62.1 |
| Compound (4) | 200 | 10 | 56.5 |
| Compound (5) | 200 | 10 | 60.0 |
| Compound (6) | 200 | 10 | 55.3 |
| Compound (7) | 200 | 10 | 65.3 |
| Compound (8) | 200 | 10 | 72.5 |
| Compound (9) | 200 | 10 | 57.2 |
| Compound (10) | 200 | 10 | 70.2 |
| Compound (11) | 200 | 10 | 65.6 |
| Compound (12) | 200 | 10 | 62.1 |
| Compound (13) | 200 | 10 | 79.2 |
| Compound (14) | 200 | 10 | 73.5 |
| Compound (15) | 200 | 10 | 77.2 |
| Gerfarnate | 300 | 10 | 33.1 |
| Cetraxate hydrochloride | 300 | 10 | 25.3 |
| Carbenoxolone sodium | 300 | 10 | 63.6 |
| Comparative compound of formula (A)-1 | 300 | 10 | 51.2 |

The results given in Pharmacological Tests 1 to 3 above show that the compound of this invention have excellent anti-peptic ulcerogenic activity.

Tests on the toxicity of the compounds of this invention and the results obtained are shown below.

TOXICITY TESTS (1) Acute toxicity test

Five STD Wistar-strain male rats (body weight 170 to 200 g) and five dd-strain male and female mice (body weight 15 to 20 g) were used. Each of the compounds (1) to (15) of this invention was orally, intravenously or subcutaneously administered to these rats and mice in a dose of 1500 mg/kg and 3000 mg/kg. But no case of death was observed.

(2) Subacute toxicity test

Ten STD Wistar-strain rats (body weight 170 to 200 g) and ten four week-old female and male mice (body weight 15 to 20 g) were used. Each of the compounds (1) to (15) was orally administered in a dose of 300 mg/kg for the rats and 25 mg/kg for the mice. The animals were allowed to take solid feeds and water freely.

As a control, a group to which no drug was administered was used.

As a result, there was no difference between the group to which the test compound was administered and the control group in regard to the increase of body weight and the amount of feeds taken.

Furthermore, no abnormality was noted in a hematological examination, a urine examination, observations in autopsy, the weights of organs and a histopathological examination.

The above test results show that the geranylgeranylacetamide compounds of formula (I) have excellent anti-ulcerogenic activity, and can be used for the prevention, therapy and repalse-prevention of ulcer as an anti-ulcerogenic agent having little side effects and high safety.

Specific examples of formulating the anti-ulcerogenic agent of this invention are shown below. It should be understood, however, that these examples are not limitative.

FORMULATION EXAMPLE 1

Injectable preparation:

The hydrochloride of compound (2) (30 mg) was dissolved in 3 ml of physiological saline and put aseptically in a 3 ml. ampoule. The ampoule was sealed up by melting and heat sterilized to form an injectable preparation which was aseptic and did not contain a pyrogenic substance.

FORMULATION EXAMPLE 2

| Tablets: | |
|---|---|
| Hydrochloride of compound (2) | 30 mg |
| Lactose | 100 mg |
| Hydroxypropyl cellulose | 2.5 mg |
| Crystalline cellulose | 20 mg |
| Talc | 1.7 mg |
| Magnesium stearate | 1.8 mg |

The above ingredients were mixed and directly tableted by a tableting machine to form tablets each weighing 150 mg.

The following examples illustrate the compounds of this invention and their production.

PRODUCTION EXAMPLE 1

A three-necked flask equipped with a thermometer and a stirrer was charged with 7.2 g of anhydrous piperazine and 100 ml of anhydrous toluene. While they were heated under reflux in an atmosphere of nitrogen, 2 g of geranylgeranylacetyl chloride was added dropwise. After the addition, the mixture was immediately cooled, and a 10% aqueous solution of sodium hydroxide was added. The organic layer was separated, washed with water and dried over anhydrous potassium carbonate. The solvent was evaporated under reduced pressure by a rotary evaporator to give a yellow oil. The yellow oil was chromatographed on a column of 800 g of silica gel using a mixture of ethyl acetate, ethanol, and n-butylamine (40:60:3 by volume) as an eluent to give 2.08 g of a purified oil. This only product was identified as N-geranylgeranylacetyl piperazine [compound (I)] by IR spectroscopy, $^1$N-NMR spectroscopy and field desorption mass spectrometry (to be abbreviated FD-MASS hereinafter; m/e values were corrected as $^1$H, $^{12}$C, $^{14}$N and $^{16}$O).

IR: ~3300, 1640, 1440, 1375, 1285, 1255, 1215, 1140, 1000 cm$^{-1}$.

$^1$H-NMR: $\delta_{ppm}^{CDCl_3}$

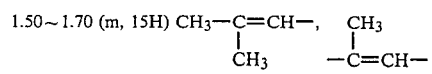

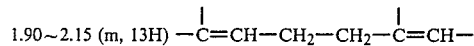

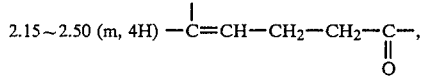

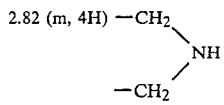

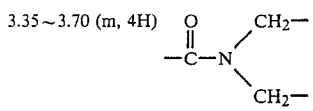

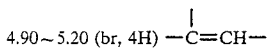

FD-MASS: m/e=400

The compound (1) was dissolved in 95% ethanol (grade stipulated in Japanese Pharmacopoeia), and an equimolar proportion of a 10% aqueous solution of sulfuric acid was added. The mixture was stirred at room temperature for 1 hour, and the solvent was evaporated under reduced pressure to give the sulfate of the compound (1). By using other acids, the corresponding hydrochloride, phosphate, citrates, lactate and glutamate were obtained by the same method as above.

PRODUCTION EXAMPLE 2

A three-necked flask equipped with a thermometer and a stirrer was charged with 69.2 g of methyl geranylgeranylacetate and 17.0 g of N-methylpiperazine. They were heated at 150° to 200° C. in an atmosphere of nitrogen for 3 hours with stirring. After cooling, the reaction mixture was chromatographed on a column of 3 kg of silica gel using a mixture of chloroform and methanol (7:1 by volume) as an eluent, and then further chromatographed on a column of 1.5 kg of silica gel using a mixture of ethyl acetate, ethanol and benzene (1:1:1 by volume) as an eluent to give 36 g of pure N-methyl-N'-geranylgeranylacetyl piperazine [compound (2)] as an oil. The structure of the product was determined from the following analytical results.

IR: 1640, 1440, 1375, 1285, 1255, 1215, 1140, 1000 cm$^{-1}$.

$^1$H-NMR: $\delta_{ppm}^{CDCl_3}$ 1.56 (s) and 1.63 (s) 15H in total

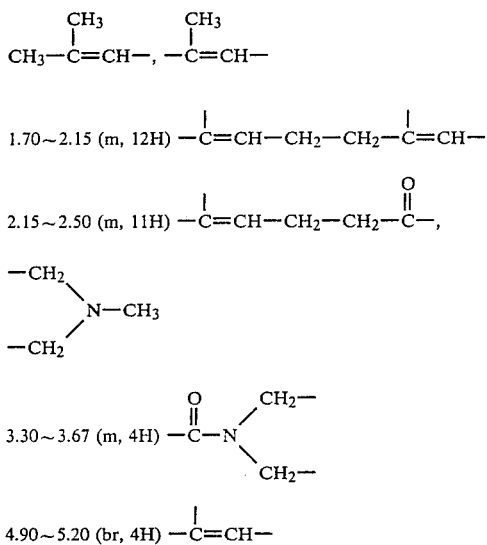

FD-MASS: m/e=414

Compound (2) obtained above was dissolved in 95% aqueous methanol, and an equimolar proportion of concentrated hydrochloric acid was added. The mixture was stirred at room temperature for 1 hour. The solvent was evaporated under reduced pressure to give the hydrochloride of the compound (2). By a similar procedure, its sulfate, phosphate, citrate and lactate were obtained by using the corresponding acids.

PRODUCTION EXAMPLE 3

Methyl geranylgeranylacetate (69.2 g) and 19.4 g of N-ethylpiperazine were reacted and worked up in the same way as in Production Example 2 to give 36 g of N-ethyl-N'-geranylgeranylacetyl piperazine [compound (3)] as an oil. The characteristic absorptions of the product in its IR spectrum nearly corresponded with those of the compound (2) obtained in Production Example 2, and its FD-MASS spectrometry gave an m/e of 428. From these facts, the structure of the product was determined.

By the same procedure as in Production Example 2, the hydrochloride, sulfate, phosphate and citrate of the compound (3) were obtained.

PRODUCTION EXAMPLE 4

Methyl geranylgeranylacetate (69.2 g) and 21.8 g of N-n-propylpiperazine were reacted and worked up in the same way as in Production Example 2 to give 37 g of N-n-propyl-N'-geranylgeranylacetyl piperazine [compound (4)] as an oil. Its structure was determined from the fact that its characteristic absorptions in its IR spectrum nearly corresponded with those of the compound (2) obtained in Production Example 2 and its FD-MASS spectrometry gave m/e=442.

By the same procedure as in Production Example 2, the hydrochloride, phosphate, citrate and lactate of the compound (4) were obtained.

PRODUCTION EXAMPLE 5

Methyl geranylgeranylacetate (69.2 g) and 21.8 g of N-isopropylpiperazine were reacted and worked up in the same way as in Production Example 2 to give 37 g of N-isopropyl-N'-geranylgeranylacetyl piperazine [compound (5)] as an oil. Its structure was determined from the fact that its characteristic absorptions in its IR spectrum nearly corresponded with those of the compound (2) obtained in Production Example 2, and its FD-MASS spectrometry gave m/e=442.

PRODUCTION EXAMPLE 6

Methyl geranylgeranylacetate (69.2 g) and 40 g of N-butylpiperazine were reacted and worked up in the same way as in Production Example 2 to give 47.8 g of N-butyl-N'-geranylgeranylacetyl piperazine [compound (6)] as an oil. The structure of the product was determined from the following analytical results.

IR: 2930, 1655, 1440 cm$^{-1}$ $^1$H-NMR: $\delta_{ppm}^{CCl_4}$

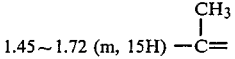

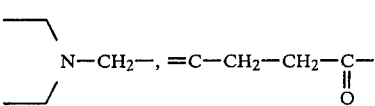

FD-MASS: m/e=456

By the same procedure as in Production Example 2, the hydrochloride, citrate, phosphate and lactate of the compound (6) were obtained.

PRODUCTION EXAMPLE 7

Methyl geranylgeranylacetate (69.2 g) and 43.4 g of N-n-amylpiperazine were reacted and worked up in the same way as in Production Example 2 to give 48.5 g of N-n-amyl-N'-geranylgeranylacetyl piperazine [compound (7)] as an oil. The structure of the product was determined from the following analytical results.

IR: 2930, 1655, 1440 cm$^{-1}$.

$^1$H-NMR: $\delta_{ppm}^{CCl_4}$

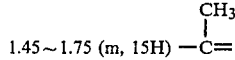

1.75~2.08 (m, 12H) =C—CH$_2$—CH$_2$—C=

2.08~3.63 (m, 14H) H on the piperazine ring,

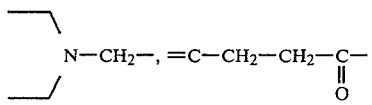

4.83~5.23 (m, 4H) —C=CH—

FD-MASS: m/e=470

By the same procedure as in Production Example 2, the hydrochloride, phosphate, citrate and lactate of the compound (7) were obtained.

PRODUCTION EXAMPLE 8

Ten grams of compound (1) synthesized as in Production Example 1, 6 g of allyl bromide and 13 g of anhydrous potassium carbonate were added to 60 ml of acetone, and heated for 5 hours in an atmosphere of nitrogen. The reaction mixture was cooled to room temperature, and the solid components were removed by filtration. The solvent was evaporated under reduced pressure by a rotary evaporator to give a yellow liquid product. The liquid product was chromatographed on a column of 500 g of silica gel using ethyl acetate as an eluent to give 8.5 g of N-allyl-N'-geranylgeranylacetyl piperazine [compound (8)]. The structure of the product was determined from the following analytical results.

IR: 2920, 1655, 1435, 995, 910 cm$^{-1}$.
NMR: $\delta_{ppm}^{CCl_4}$ 1.3~1.75 (m, 15H) —C=CH$_3$ 1.75~2.1 (m, 12H) =C—CH$_2$—CH$_2$—C=

2.1~3.65 (m, 14H) H on the piperazine ring,

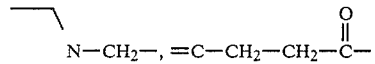

4.8~5.3 (m, 6H) —C=CH—, CH=CH$_2$ 5.65~6.40 (m, 1H) —CH=CH$_2$

FD-MASS: m/e=440

By the same procedure as in Production Example 1, the sulfate, hydrochloride, phosphate and citrate of the compound (8) were obtained.

PRODUCTION EXAMPLE 9

The same reaction and work-up as in Production Example 8 were carried out using 10 g of compound (1) synthesized as in Production Example 1, 5 g of prenyl chloride, 12 g of anhydrous potassium carbonate and 50 ml of acetone. There was obtained 8.7 g of N-prenyl-N'-geranylgeranylacetyl piperazine [compound (9)] as an oil. The structure of the product was determined from the following analytical results.

IR: 2920, 1655, 1438 cm$^{-1}$.
NMR: $\delta_{ppm}^{CCl_4}$ 1.3~1.75 (m, 21H) —C=CH$_3$ 1.75~2.1 (m, 12H) =C—CH$_2$—CH$_2$—C=

2.1~3.65 (m, 14H) H on the piperazine ring,

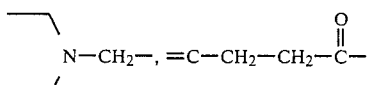

4.8~5.3 (m, 5H) —C=CH—

FD-MASS: m/e=468

By the same procedure as in Production Example 1, the sulfate, hydrochloride, phosphate, citrate and lactate of the compound (9) were obtained.

PRODUCTION EXAMPLE 10

The same reaction and work-up as in Production Example 8 were carried out using 10 g of compound (1) synthesized as in Production Example 1, 8.5 g of tetramethylene chlorobromide, 13 g of anhydrous potassium carbonate and 60 ml of acetone. There was obtained 4.2 g of N-4-chlorobutyl-N'-geranylgeranylacetyl piperazine [compound (10)] as an oil. The structure of the product was determined from the following analytical results.

IR: 2920, 1645, 1435 cm$^{-1}$.
$^1$H-NMR: $\delta_{ppm}^{CCl_4}$ 1.40~1.20 (m, 19H) —C=CH$_3$, N—C—CH$_2$—CH$_2$—C—Cl 1.8~2.1 (m, 12H) =C—CH$_2$—CH$_2$—C=
2.1~3.63 (m, 16H) H on the piperazine ring,

=C—CH$_2$—CH$_2$—C—
∥
O

—CH$_2$—Cl, 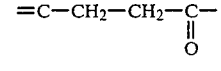

4.80~5.25 (m, 4H) =CH—

FD-MASS: m/e=490

By the same procedure as in Production Example 2, the hydrochloride, phosphate and citrate of the compound (10) were obtained.

PRODUCTION EXAMPLE 11

The same reaction and work-up as in Production Example 8 were carried out using 10 g of compound (1) synthesized as in Production Example 1, 10 g of 1,3-dibromopropane, 10 g of anhydrous potassium carbonate, 0.1 g of potassium iodide and 50 ml of acetone. There was obtained 4.7 g of N-3-bromopropyl-N'-geranylgeranylacetyl piperazine [compound (11)] as an oil. The structure of the product was determined from the following analytical results:

IR: 2920, 1650, 1438 cm$^{-1}$.
$^1$H-NMR: $\delta_{ppm}^{CCl_4}$ 1.45~1.75 (m, 15H) $-\overset{\underset{\displaystyle |}{CH_3}}{C}=$ 1.75~2.1 (m, 14H) $=C-CH_2-CH_2-C=$ 2.1~2.25 (m, 4H) $=C-CH_2-CH_2-\underset{\underset{\displaystyle O}{\|}}{C}-$ 2.25~3.67 (m, 14H) H on the piperazine ring, $\diagdown$
   $N-CH_2-, -CH_2-Br$
$\diagup$ 4.85~5.25 (m, 4H) $-\overset{|}{C}=CH-$ FD-MASS: m/e=520

By the same procedure as in Production Example 2, the hydrochloride, phosphate, citrate and lactate of the compound (11) were obtained.

PRODUCTION EXAMPLE 12

The same reaction and work-up as in Production Example 2 were carried out using 69.2 g of methyl geranylgeranylacetate and 41.7 g of N-benzylpiperazine to give 52.4 g of N-benzyl-N'-geranylgeranylacetyl piperazine [compound (12)] as an oil. The structure of the product was determined from the following analytical results.

IR: 2910, 1653, 1435 cm$^{-1}$.
$^1$H-NMR: $\delta_{ppm}^{CCl_4}$ 1.5~1.7 (m, 15H) $-\overset{\underset{\displaystyle |}{CH_3}}{C}=$ 1.8~2.15 (m, 12H) $=C-CH_2-CH_2-C=$ 2.15~2.3 (m, 4H) $=C-CH_2-CH_2-\underset{\underset{\displaystyle O}{\|}}{C}-$ 2.33~3.6 (m, 10H) H on the piperazine ring, $-CH_2-Ph$ 4.9~5.25 (m, 4H) $-\overset{|}{C}=CH-$ 7.25 (s, 5H) H on the benzene ring FD-MASS: m/3=490

By the same procedure as in Production Example 2, the hydrochloride, phosphate, citrate and lactate of the compound (12) were obtained.

PRODUCTION EXAMPLE 13

The same reaction and work-up as in Production Example 2 were carried out by using 69.2 g of methyl geranylgeranylacetate and 35.0 g of 2-methylpiperazine to give 59.2 g of methyl-N-geranylgeranylacetyl piperazine [compound (13)] as an oil. The structure of the product was determined from the following analytical results.

IR: 3310, 2910, 1640, 1438 cm$^{-1}$.
$^1$H-NMR: $\delta_{ppm}^{CCl_4}$ 1.0 (d, 3H) $N\diagup\overset{CH_3}{\diagdown}N$ (piperazine ring)

1.4~1.7 (m, 15H) $-\overset{\underset{\displaystyle |}{CH_3}}{C}=$ 1.8~2.1 (m, 12H) $=C-CH_2-CH_2-\overset{|}{C}=$ 2.1~2.35 (m, 4H) $=C-CH_2-CH_2-\underset{\underset{\displaystyle O}{\|}}{C}-$ 2.4~4.35 (m, 8H) H on the piperazine ring 4.85~5.25 (m, 4H) $-\overset{|}{C}=CH-$ FD-MASS: m/e=414

By the same procedure as in Production Example 2, the hydrochloride, phosphate, citrate and lactate of the compound (13) were obtained.

PRODUCTION EXAMPLE 14

The same reaction and work-up as in Production Example 2 were carried out using 69.2 g of methyl geranylgeranylacetate and 40.0 g of 2-ethylpiperazine to give 60.5 g of ethyl-N-geranylgeranylacetyl piperazine [compound (14)] as an oil. The structure of the product was determined from the following analytical results.

IR: 3310, 2910, 1640, 1438 cm$^{-1}$.
$^1$H-NMR: $\delta_{ppm}^{CCl_4}$ 0.95 (t, 3H) $-C-CH_3$ 1.2~1.7 (m, 17H) $-\overset{\underset{\displaystyle |}{CH_3}}{C}=, C-CH_2-CH_3$ 1.8~2.1 (m, 12H) $=C-CH_2-CH_2-\overset{|}{C}=$ 2.1~2.35 (m, 4H) $=C-CH_2-CH_2-\underset{\underset{\displaystyle O}{\|}}{C}-$ 2.4~4.6 (m, 7H) H on the piperazine ring 4.85~5.23 (m, 4H) $-\overset{|}{C}=CH-$ FD-MASS: m/e=428.

By the same procedure as in Production Example 2, the hydrochloride, phosphate, citrate and lactate of the compound (14) were obtained.

PRODUCTION EXAMPLE 15

The same reaction and work-up as in Production Example 2 were carried out using 69.2 g of methyl geranylgeranylacetate and 21.5 g of 2,6-dimethylpiperazine to give 38.4 g of 2,6-dimethyl-N-geranylgeranylacetyl piperazine [compound (15)] as an oil. The structure of the product was determined from the following analytical results.

IR: 2922, 1645, 1437 cm$^{-1}$.

NMR: $\delta_{ppm}^{CCl_4}$

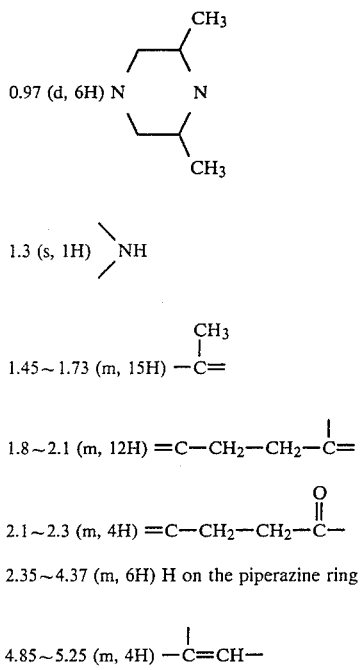

0.97 (d, 6H)

1.3 (s, 1H) NH 1.45~1.73 (m, 15H) —C(CH₃)=

1.8~2.1 (m, 12H) =C—CH₂—CH₂—C=

2.1~2.3 (m, 4H) =C—CH₂—CH₂—C(=O)—

2.35~4.37 (m, 6H) H on the piperazine ring 4.85~5.25 (m, 4H) —C=CH—

FD-MASS: m/e=428

By the same procedure as in Production Example 2, the hydrochloride, phosphate, citrate and lactate of the compound (15) were obtained.

What is claimed is:

1. A geranylgeranylacetamide compound having a piperazine ring represented by the formula

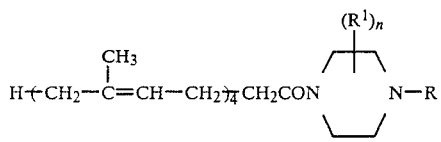

wherein R represents a member selected from the class consisting of a hydrogen atom, $C_1$–$C_5$ alkyl groups which are unsubstituted or mono-substituted by a halogen atom, $C_2$–$C_5$ alkenyl groups and $C_7$–$C_8$ aralkyl groups, $R^1$ represents a $C_1$–$C_3$ alkyl group and n represents 0, 1 or 2, or a pharmaceutically acceptable acid addition salt thereof.

2. A compound or its salt according to claim 1 wherein the compound of formula (I) is N-geranylgeranylacetyl piperazine.

3. A compound or its salt according to claim 1 wherein the compound of formula (I) is N-methyl-N'-geranylgeranylacetyl piperazine.

4. A compound or its salt according to claim 1 wherein the compound of formula (I) is N-ethyl-N'-geranylgeranylacetyl piperazine.

5. A compound or its salt according to claim 1 wherein the compound of formula (I) is N-n-propyl-N'-geranylgeranylacetyl piperazine.

6. A compound or its salt according to claim 1 wherein the compound of formula (I) is N-iso-propyl-N'-geranylgeranylacetyl piperazine.

7. A compound or its salt according to claim 1 wherein the compound of formula (I) is N-n-butyl-N'-geranylgeranylacetyl piperazine.

8. A compound or its salt according to claim 1 wherein the compound of formula (I) is N-n-pentyl-N'-geranylgeranylacetyl piperazine.

9. A compound or its salt according to claim 1 wherein the compound of formula (I) is N-allyl-N'-geranylgeranylacetyl piperazine.

10. A compound or its salt according to claim 1 wherein the compound of claim (I) is N-prenyl-N'-geranylgeranylacetyl piperazine.

11. A compound or its salt according to claim 1 wherein the compound of formula (I) is N-4-chlorobutyl-N'-geranylgeranylacetyl piperazine.

12. A compound or its salt according to claim 1 wherein the compound of formula (I) is N-3-bromopropyl-N'-geranylgeranylacetyl piperazine.

13. A compound or its salt according to claim 1 wherein the compound of formula (I) is N-benzyl-N'-geranylgeranylacetyl piperazine.

14. A compound or its salt according to claim 1 wherein the compound of formula (I) is 2-methyl-N-geranylgeranylacetyl piperazine.

15. A compound or its salt according to claim 1 wherein the compound of formula (I) is 2-ethyl-N-geranylgeranylacetyl piperazine.

16. A compound or its salt according to claim 1 wherein the compound of formula (I) is 2,6-dimethyl-N-geranylgeranylacetyl piperazine.

17. A pharmaceutical composition for treatment of peptic ulcer, said composition being composed of (1) an amount, effective for treatment of peptic ulcer, of a geranylgeranylacetamide compound having a piperazine ring represented by the formula

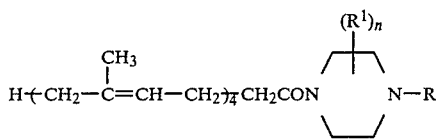

wherein R represents a member selected from the class consisting of a hydrogen atom, $C_1$–$C_5$ alkyl groups which are unsubstituted or mono-substituted by a halogen atom, $C_2$–$C_5$ alkenyl groups and $C_7$–$C_8$ aralkyl groups, $R^1$ represents a $C_1$–$C_3$ alkyl group and n is 0, 1, or 2, or a pharmaceutically acceptable acid addition salt thereof, and (2) a pharmaceutically acceptable diluent or carrier.

18. A method for the treatment of an ulcer in a mammal, which comprises administering to said subject an effective amount of a geranylgeranylacetamide compound having a piperazine ring represented by the formula

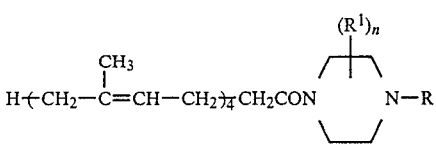

wherein R represents a member selected from the class consisting of a hydrogen atom, $C_1$–$C_5$ alkyl groups which are unsubstituted or mono-substituted by a halogen atom, $C_2$–$C_5$ alkenyl groups and $C_7$–$C_8$ aralkyl groups, $R^1$ represents a $C_1$–$C_3$ alkyl group and n is 0, 1, or 2, or a pharmaceutically acceptable acid addition salt thereof.

* * * * *